United States Patent
Bressler et al.

(10) Patent No.: US 9,051,080 B2
(45) Date of Patent: Jun. 9, 2015

(54) SINGLE-DOSE PACKAGE

(75) Inventors: Christian Bressler, Basel (CH); Marcus Hoffmann, Usingen (DE)

(73) Assignee: Heraeus Kulzer GmbH, Hanau (DE)

( * ) Notice: Subject to any disclaimer, the term of this patent is extended or adjusted under 35 U.S.C. 154(b) by 1552 days.

(21) Appl. No.: 12/240,349

(22) Filed: Sep. 29, 2008

(65) Prior Publication Data

US 2009/0084690 A1    Apr. 2, 2009

(30) Foreign Application Priority Data

Sep. 28, 2007  (DE) .......................... 10 2007 046 898
Dec. 5, 2007   (DE) .......................... 10 2007 058 924

(51) Int. Cl.
  *A61C 19/02*   (2006.01)
  *B65D 8/00*    (2006.01)
  *A61C 5/06*    (2006.01)

(52) U.S. Cl.
  CPC ............... *B65D 11/02* (2013.01); *A61C 5/066* (2013.01); *B65D 2221/00* (2013.01)

(58) Field of Classification Search
  CPC ..... A61C 5/066; B65D 11/02; B65D 2221/00
  USPC ............ 206/63.5, 368, 209, 209.1, 369, 438; 433/80, 89, 90, 82, 126, 215; 401/126, 401/132; 222/153.07
  See application file for complete search history.

(56) References Cited

U.S. PATENT DOCUMENTS

| | | | | |
|---|---|---|---|---|
| 3,204,835 A | | 9/1965 | Michel | |
| 3,785,481 A | * | 1/1974 | Allet-Coche | 206/219 |
| D287,876 S | * | 1/1987 | Blatherwick et al. | D24/114 |
| 5,169,315 A | * | 12/1992 | Bull | 433/163 |
| 5,396,986 A | * | 3/1995 | Fountain et al. | 206/219 |
| 5,860,806 A | * | 1/1999 | Pranitis et al. | 433/80 |
| 6,439,380 B1 | * | 8/2002 | Welsh | 206/219 |
| 6,450,717 B1 | * | 9/2002 | Salz et al. | 401/125 |
| 6,726,005 B2 | * | 4/2004 | Lentine | 206/222 |
| 7,112,062 B2 | * | 9/2006 | Lee | 433/89 |
| 2001/0015326 A1 | * | 8/2001 | Bleuer | 206/63.5 |
| 2002/0027088 A1 | * | 3/2002 | Discko, Jr. | 206/229 |
| 2007/0187265 A1 | * | 8/2007 | Hohmann et al. | 206/63.5 |

FOREIGN PATENT DOCUMENTS

DE        4216913 A1    11/1993
DE    202006002646 U1    6/2006

OTHER PUBLICATIONS

English Language Abstract for DE 42 16 913 A1.
English Language Abstract for DE 20 2006 002 646 U1.

* cited by examiner

*Primary Examiner* — Steven A. Reynolds

(74) *Attorney, Agent, or Firm* — Norris McLaughlin & Marcus, P.A.

(57) ABSTRACT

The invention relates to a single-dose package for liquid, pasty or semi-solid materials, with a fluid container of at least one lower and at least one upper partial container, whereby, after filling, the at least one lower partial container is provided to be connected at a common seam to the at least one upper partial container such that the upper partial container sits on top of the lower partial container at the seam, and the upper partial container carries a removal spout, on which a circumferential splash protection neck is provided.

15 Claims, 4 Drawing Sheets

SINGLE-DOSE PACKAGE

BACKGROUND OF THE INVENTION

The invention relates to a single-dose package for liquid, pasty or semi-solid materials, preferably for dental material, having a fluid container of at least one lower and at least one upper partial container, wherein, after filling, the at least one lower partial container is provided to be connected at a common seam to the at least one upper partial container such that the upper partial container sits on top of the lower partial container at the seam, and the upper partial container carries a removal spout, preferably for dental material.

Liquid dental materials are often applied to the teeth to be treated using paint brushes or brushes ("Microbrush®"). It is important in this context that the handling is easy and the liquid can be removed and applied, if at all possible, using only one hand. This is less of a problem if the material is to be removed from bottles. However, dental materials are often supplied in so-called "single-dose" packages, in which one portion each gets freshly opened, while the remaining portions are protected from perishing or contamination. Small packages of this type can also be provided with a suitable support base.

A single-dose package with support base at the lower end of the fluid container and handle for twist-off of the upper end of the fluid container is known. The twisting-off opens the container at a predetermined breakage site such it is accessible for a removal instrument (e.g. Microbrush®). However, some of the liquid content may splash in an uncontrolled manner during twist-off, especially when, e.g., the warmth of the hand caused an over-pressure to be built-up in the container.

The invention remedies this problem in that it provides a circumferential splash protection.

BRIEF SUMMARY OF THE INVENTION

The package according to the invention comprises at least two partial containers that sit one on top of the other. These need not be of equal size and may take up different volumes. The simplest case is to have two partial containers. Connected to each other along a seam that is preferably ultrasound-welded, they jointly form a fluid container. The lower partial container can be connected to a support base, the upper partial container carries a removal spout. The removal spout can be opened along a predetermined breakage site by means of a twist-off handle. The content of the package can suitably be removed through the spout using a removal instrument. A circumferential splash protection neck, which is capable of catching material leaking inadvertently from the predetermined breakage site, is provided on the removal spout. It can be connected to the spout or the twist-off handle.

Accordingly, the invention relates to a package according to Claim 1. Preferred embodiments are evident from the other claims.

BRIEF DESCRIPTION OF THE SEVERAL VIEWS OF THE DRAWING(S)

The invention is illustrated based on the following figures. In the figures:

FIG. 1 shows a cross-section through a closed single-dose package. The fluid is not shown. The space, in which a Microbrush® (14) can be moved in order to remove the fluid, is shown.

DETAILED DESCRIPTION OF THE INVENTION

Figure 1:
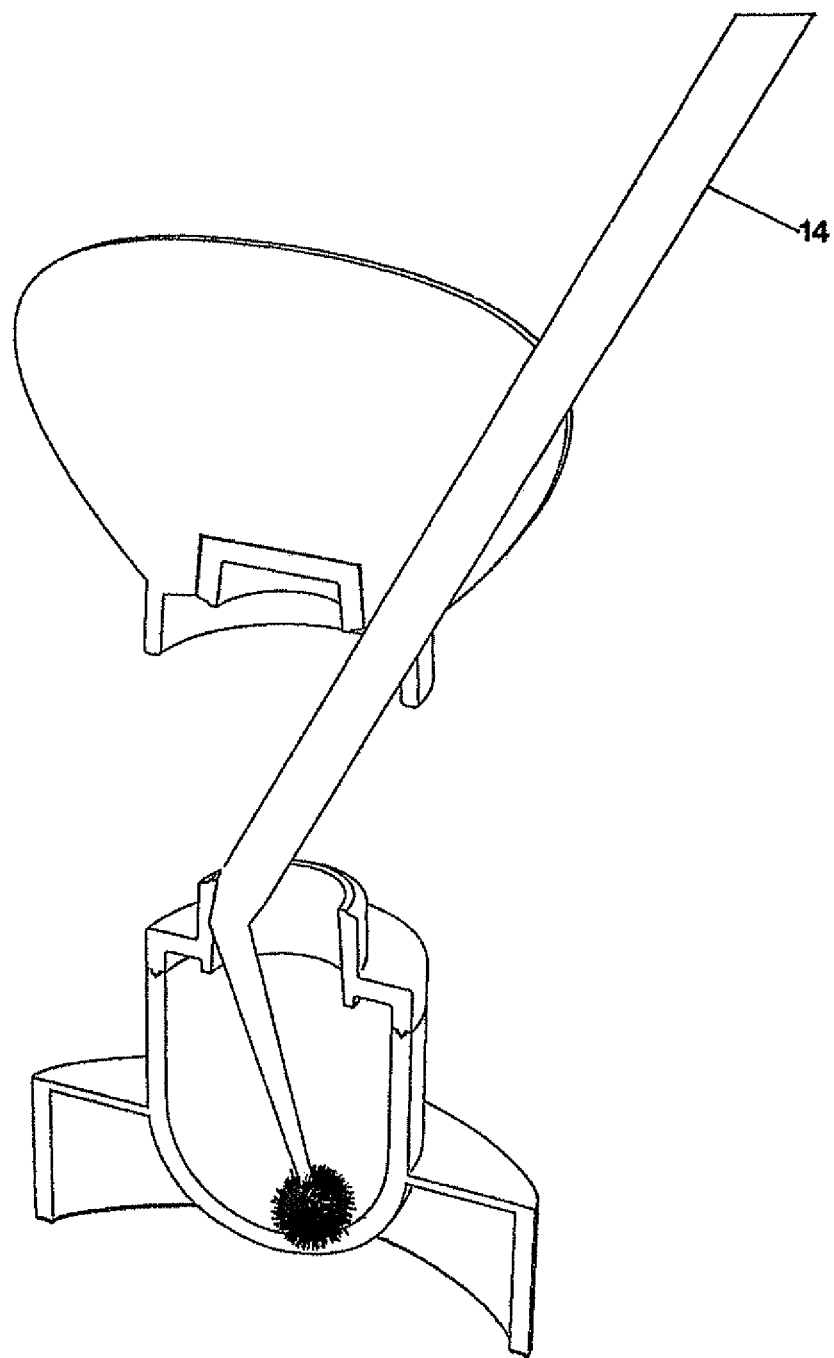
Figure 2:
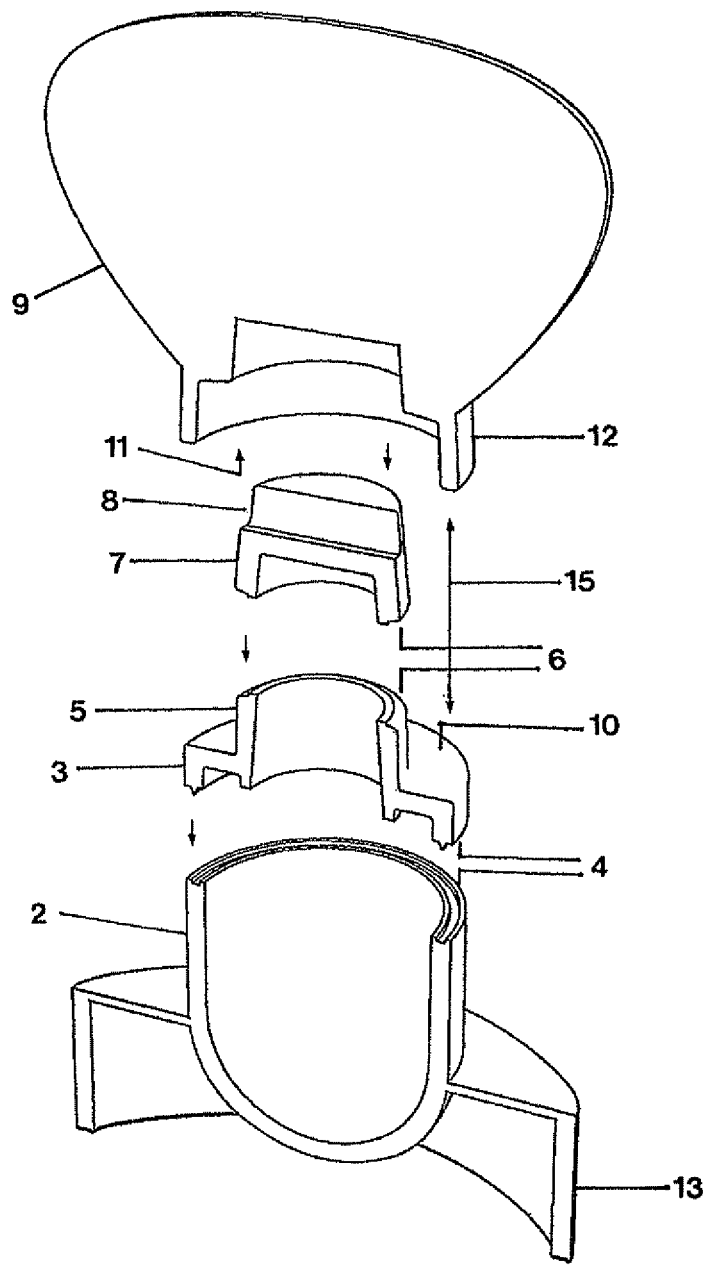
FIG. 2 shows the individual parts from which a single-dose package is assembled.
Figure 3:
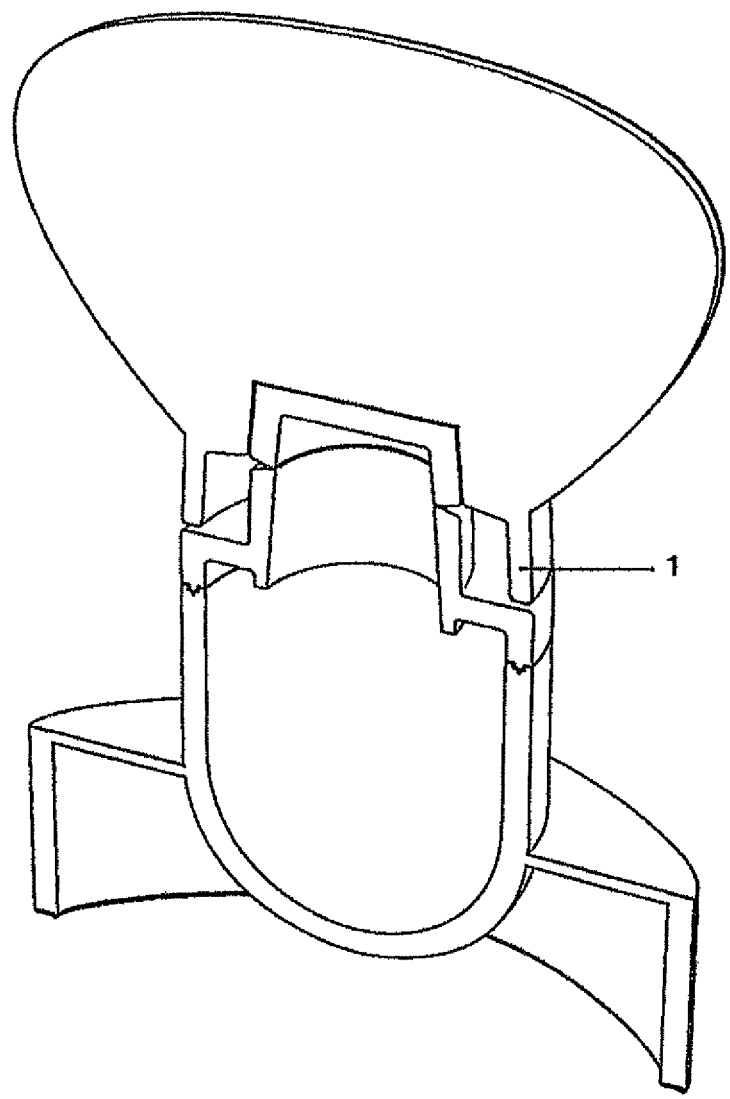
FIG. 3 shows in yet another view where the pressure can escape and which space is limited by the splash protection.
Figure 4:
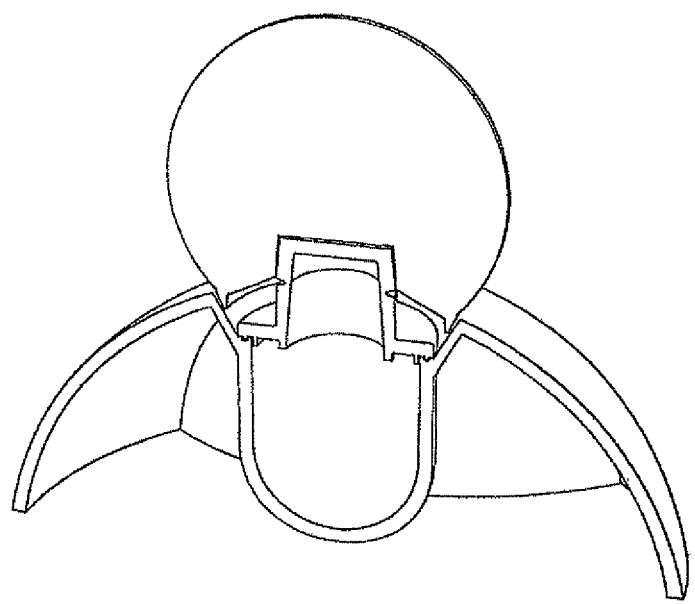
FIG. 4 shows yet another cross-section with a support base of different design.

In an exemplary embodiment of the invention, the fluid container 1 consists of a lower 2 and an upper 3 partial container that are being connected to each other by ultrasound welding after they are filled. The non-closed lower partial container 2 comprises the shape of a cylinder with semi-spherical bottom. It is preferably connected to a support base. This can be designed to be elliptical in order to form a suitable hold-up with respect to the twist-off handle. When the lower partial container gets closed, another cylinder (upper partial container 3), which carries a removal spout 5 with predetermined breakage site 6 and cap 7 with reception groove 8 for the twist-off handle 9, is placed on the seam 4. The diameter of the removal spout 5 is approximately half of that of the cylinders. The removal spout 5 is carried by a stepped ring 10 which, jointly with the removal spout 5, forms the upper margin of the fluid container 1 perpendicular to the cylinder wall. The seam 4 is provided for welding, e.g. friction welding or ultrasound welding. The twist-off handle 9 carries a spring 11 that is complementary to the reception groove 8 and is connected to another circumferential splash protection cylinder 12 whose diameter corresponds to that of the other cylinders and which sits on top of the stepped ring 10.

The tool needed for welding, e.g. a sonotrode, can be guided within the space 15 between the circumferential splash protection cylinder and the removal spout.

The package is suitable for any liquids, pastes or semi-solid materials, for which packaging in single-doses is reasonable. This includes, in particular, liquids that tend to dry up in re-closeable containers or cause crusts to form on the closure. This is a problem, e.g., in the case of nail polish, correction fluid, mascara, and paint for artists. It is also conceivable to fill instant glue or 2-component glue into the package according to the invention. The package is also suitable for paste material that is applied in small doses and would be removed, e.g., with a spatula. The user can remove the material and/or liquid using a suitable removal instrument, for example a paint brush, Microbrush®, spoon or spatula.

The corresponding removal instrument can be provided on the package such that it is easy to detach therefrom.

The invention claimed is:

1. A single-dose package for liquid, pasty or semi-solid materials, comprising
a fluid container including a lower and an upper partial container, wherein, after filling, the lower partial container is provided to be connected at a common seam to the upper partial container such that the upper partial container sits on top of the lower partial container at the seam, and the upper partial container carries a removal spout, and wherein a circumferential splash protection neck is provided on the removal spout.

2. The single-dose package according to claim 1, wherein the removal spout (5) is surrounded by a covering surface (10) which, jointly with the removal spout (5), forms an upper margin of the fluid container (1) perpendicular to a lateral wall of the lower (2) and/or upper (3) partial container.

3. The single-dose package according to claim 2, wherein the splash protection neck sits on top of the covering surface (10).

4. The single-dose package according to claim 1, wherein the lower partial container takes the shape of a cylinder with a bottom that is level or deviates from being level in shape.

5. The single-dose package according to claim 1, wherein the removal spout is provided with predetermined breakage site and cap and can be connected to a twist-off handle.

6. The single-dose package according to claim 5, wherein the twist-off handle or the removal spout are connected to the circumferential splash protection neck.

7. The single-dose package according to claim 2, wherein the diameter of the removal spout (5) is approximately half of the diameter of the lower partial container.

8. The single-dose package according to claim 5, wherein the cap (7) comprises a reception groove for the twist-off handle and the twist-off handle comprises a spring that is complementary to the reception groove.

9. The single-dose package according to claim 2, wherein the covering surface takes the shape of a perforated disc.

10. The single-dose package according to claim 6, wherein the splash protection is a cylindrical neck.

11. The single-dose package according to claim 2, wherein the lower partial container is connected to a support base.

12. The single-dose package according to claim 11, wherein a horizontal projection of the support base deviates from circular shape in order to form a suitable hold-up with respect to the twist-off handle.

13. The single-dose package according to claim 1, further comprising a recess is provided, in which a removal instrument is attached such that it is easy to detach.

14. The single-dose package according to claim 4, wherein the removal instrument (14) is a paint brush, spatula, spoon or liquid applicator for dentistry.

15. The single-dose package according to claim 1, further comprising a liquid dental material.

* * * * *

UNITED STATES PATENT AND TRADEMARK OFFICE
CERTIFICATE OF CORRECTION

PATENT NO.      : 9,051,080 B2
APPLICATION NO. : 12/240349
DATED           : June 9, 2015
INVENTOR(S)     : Bressler et al.

Page 1 of 1

It is certified that error appears in the above-identified patent and that said Letters Patent is hereby corrected as shown below:

In the claims

Col. 4, claim 14, line 12, change "4" to --13--.

Signed and Sealed this
Fourteenth Day of June, 2016

Michelle K. Lee
*Director of the United States Patent and Trademark Office*